United States Patent [19]

Schmidt

[11] Patent Number: 4,925,670

[45] Date of Patent: May 15, 1990

[54] ADMINISTRATION AND DOSAGE FORM FOR DRUG ACTIVE AGENTS, REAGENTS OR THE LIKE AND PROCESS FOR THE PREPARATION THEREOF

[75] Inventor: Wolfgang Schmidt, Hamburg, Fed. Rep. of Germany

[73] Assignee: Desitin Arzneimittel GmbH, Hamburg, Fed. Rep. of Germany

[21] Appl. No.: 344,519

[22] Filed: Apr. 24, 1989

Related U.S. Application Data

[63] Continuation of Ser. No. 94,442, Sep. 9, 1987, abandoned.

[30] Foreign Application Priority Data

Sep. 9, 1986 [DE] Fed. Rep. of Germany ....... 3630603

[51] Int. Cl.⁵ .............................................. A61L 9/70
[52] U.S. Cl. ..................................... 424/443; 424/487
[58] Field of Search ............................... 424/409, 411

[56] References Cited

U.S. PATENT DOCUMENTS

| | | | |
|---|---|---|---|
| 4,008,351 | 2/1977 | Inoue et al. | 424/414 |
| 4,136,162 | 1/1979 | Fuchs et al. | 514/152 |
| 4,197,289 | 4/1980 | Sturzenegger et al. | 424/443 |
| 4,451,260 | 5/1984 | Mitra | 424/444 |
| 4,483,846 | 11/1984 | Koide et al. | 424/443 |

FOREIGN PATENT DOCUMENTS

| | | | |
|---|---|---|---|
| 637363 | 9/1963 | Belgium . | |
| 1434042 | 4/1926 | United Kingdom | 424/414 |

*Primary Examiner*—Ellis P. Robinson
*Assistant Examiner*—Leon R. Horne
*Attorney, Agent, or Firm*—Cushman, Darby & Cushman

[57] ABSTRACT

A novel dosage form for drug active agents, reagents or other active agents comprising a film-like carrier material having an active agent-containing coating one side thereof and wherein the carrier material is in the form of a release paper, film or foil, and the active agent-containing coating is removed in a dosewise manner from the carrier material after subdivision into dosage units. The removed active agent-containing portions are suitable as oral drugs, pharmaceuticals, reagents or foodstuff.

9 Claims, No Drawings

ADMINISTRATION AND DOSAGE FORM FOR DRUG ACTIVE AGENTS, REAGENTS OR THE LIKE AND PROCESS FOR THE PREPARATION THEREOF

This is a continuation of application Ser. No. 94,442, filed Sept. 9, 1987, now abandoned.

BACKGROUND OF THE INVENTION

Drugs, pharmaceuticals or medicaments can be orally administered in the form of powders, dropping solutions or juices. However, as the precise dosage is difficult to determine using these forms for administering drugs, manufacturers generally give preference to dosage forms, such as tablets, dragees or capsules. Reagents and other active agents, e.g. sweeteners are frequently tabletted for precise dosage use. Although methods for the production of tablets, dragees, capsules and the like have been developed to a very advanced degree, it is impossible to overlook a number of problems associated with these dosage forms.

When low doses of active agents are to be administered a considerable amount of adjuvant must be present in order that the preparation given is of a manageable size. Further, since it is virtually impossible to accurately mark individual tablets or dragees, blister packs containing a large number of tablets, dragees and capsules, have become widely used and are printed with the necessary information, such as the name of the product. However, the production of such packs requires an additional operation. In addition, the packs require further packaging in the form of folding boxes which have a considerable empty volume and therefore take up additional storage space.

A particular disadvantage associated with dragees and capsules is that it is virtually impossible to split them, so that the smallest dose must always be predetermined. Even in the case of tablets, only larger tablets with a notch or groove at the predetermined breaking point can be divided or split, but this often results in fragments of unequal size.

Attempts have been made to provide a new dosage form for orally administered drugs that is, active agent-containing films. Belgian Patent No. 637,363 discloses a paper-like carrier material of insoluble cellulose fibers, impregnated or coated with an active agent solution. The carrier film is perforated, in the manner of a sheet of postage stamps, in order to provide individual doses. German Patent Nos. DE-OS 24 32 925 and DE-OS 24 49 865 disclose incorporating drug active agents into film formers, preferably comprising water-soluble compounds, such as methyl and ethyl cellulose. Hydroxypropyl cellulose, hydroxyethyl cellulose and methyl hydroxypropyl cellulose can also be used. The thus obtained active agent-containing film can also be subdivided by perforation into individual portions for dosage purposes.

These proposals have not been used in practice and no mention is made thereof in "Arzneiformenlehre" by P. H. List, 4th edition, Stuttgart, 1985. This is due to the fact that the necessary weight constancy and uniform active agent distribution have not been achieved.

For example, Ph. Eur., fixes criteria for weight uniformity of individually dosed medicaments, in which the latter are graduated in accordance with the particular average weight on the basis of maximum admissible divergences in %, that is ±5 to 10%. There are also corresponding values for solid medicaments relating to other parameters, such as the disintegration time and rate of dissolution.

The aforementioned proposals result in products which are difficult to ingest and are inconsistent as to dosage per surface unit. Further, when incorporating an active agent into a film, not only does the problem of precise dosage occur, but a corresponding film must be produced separately for each active agent. Thus, the production process is not advantageous from an economical standpoint.

SUMMARY OF THE INVENTION

The present invention provides a "two-dimensional" dosage form which does not exhibit the aforementioned disadvantages and which can be easily manufactured and adapted with maximum flexibility to the requirements of the market and different active agents.

DETAILED DESCRIPTION OF THE INVENTION AND EXAMPLES

According to the present invention there is provided a dosage form for drug active agents, reagents or the like, comprising a film-like carrier material having an active agent-containing coating on one side thereof, wherein said carrier material is a release paper, a release film or a release foil and said active agent-containing coating, is removed dosewise from the carrier material following subdivision into dosage units.

The novel dosage form has a number of important advantages.

Since the carrier does not form part of the dosage form itself, it has the necessary strength, without impairing the acceptance of the medicament by the patient. In the case of highly active drugs, the active agent-containing coating can be very thin, because the carrier material ensures the necessary mechanical strength.

Further, with the aid of modern application processes, the active agent-containing coating can be applied with a constant thickness.

If sterilization is necessary, this can be achieved without difficulty by radiation treatment as a result of the limited coating thickness.

The carrier can be printed at the front and particularly the back with various information, and as a result of the relatively large surface of, for example, 4 to 10 cm$^2$, detailed information for the patient can be printed on the uncoated carrier material.

In addition, the dosage units can be subdivided or split, so that only one product need be produced for different dosages (e.g. for adults and children). However, the prior subdivision can be carried out by the pharmacist or in hospitals in accordance with the doctor's prescription.

The novel dosage requires very little space. Thus, in place of folding boxes, it is possible to use bags or pouches made from plastic film or plastic-coated paper, into which the product is sealed, in much the same way as moist refreshing cloths or towelettes.

Various materials can be used as the carrier, e.g. papers weighing approximately 80 to 120 g/m$^2$ preferably 100 g/m$^2$, plastic film or sheets comprising polyethylene, polyvinylchloride, polyvinylidenechloride, polyester and other inert polymers or thin metal foils, for example, those made from aluminum. Preference is given to siliconized papers, which are commercially available, and are used for covering self-adhesive products such as plasters, adhesive tapes or adhesive labels. Wax or paraffin-coated release papers have largely been replaced by inert silicone-coated papers. When the active agent-containing coating is only applied to one carrier film side, only the latter is provided with a non-adhesive coating. The back surface should preferably be such that it can be easily and durably printed with different types of information.

The possibility of printing the back and front surfaces is a particular advantage of the novel dosage form. For example, it is possible to print the name, details concerning the constituents and dosage information on these surfaces. It would even be possible to print the entire content of a pack-in label on the back, so that there would be no need for such a label, which is frequently lost during shipping and handling. In the case of drugs which have to be taken regularly, e.g. hormonal contraceptives, the complete administration plan can be provided in such a way that a simple ingestion check is ensured. As the individual dosage units are removed from the carrier, the latter remains in existence until the drug has been completely used up. Thus, none of the printed information is lost.

Preferably an aqueous coating substance is used for the active agent-containing coating. This substance is physiologically inert and comprises components which are suitable for drug and food use. The coating substance can comprise water soluble swelling agents in the form of polymeric film formers, preferably gelatin, celluloses or hemicelluloses and swelling or soluble starches.

Preferably, plasticizers are also added, preferably polyhydric alcohols, such as glycerol or sorbitol. In addition, for setting the desired viscosity of the coating substance, polymeric swelling agents, preferably alginates, pectins, chitins, lecithins or polyethylene glycols can be used. The latter substances can simultaneously serve as an adhesive. Water-soluble gums or gum arabic can be added in order to improve the adhesion of the coating to the carrier material. Finally, preservatives, such as e.g. p-hydroxybenzoates, dyes (food dyes), pigments, such as titanium dioxide, or flavouring and sweetening agents can be added.

Advantageously coating masses with a water content of approximately 50% and a viscosity of approximately 30 to 10.000 cPs are used. The formulation and preparation are similar to those of a medicinal juice, in which the active substance or active substance combination is dissolved or uniformly dispersed. The coating material must have an adequate homogeneity and galenic stability, so that a uniform active substance content of the finished coating is ensured.

| Gelatin | 8 to 10 g |
|---------|-----------|
| Starch | 3 to 8 g |
| Glycerol | 1 to 2 g |
| Water | 30 to 50 g |

The active agent is dissolved or dispersed in this basic substance. When using a dispersion to achieve a uniform distribution, the active agent must be finely divided, preferably the average particle size is in the range of approximately 1 to 20 μm.

The desired active agent dose and the surface of the dosage units determine the thickness of the coating. Further, the moisture content of the coating substance and the finished coating, must be taken into consideration.

The coating substance can also be processed to an active agent-containing film and then coated on the carrier material, optionally using a physiologically inert adhesive. This embodiment is particularly useful if the active agent-containing coating is to have a greater thickness, so that processing to a film is possible.

The novel dosage form is particularly suitable for drugs which have to be administered in low dosages, for example, in which the single dose for oral administration is between 0 mg (placebo) and approximately 20 mg. Suitable drug active agents occur in all fields of oral therapy, especially, analeptics, antibiotics, antidiabetics, antiemitics, antiepileptics, antihypertonics, corticoids, geriatrics, hypnotics, cardiacs, hypostatics and biological active substances.

The coating can contain one or more drug active agents. If several active agents are used that are not intercompatible with each other it is possible to apply the coating in several layers each having a different composition. The agents can be applied so that the active agents are separated from one another. If necessary an active agent-free intermediate layer can be provided. A further protective layer can be applied over the active agent-containing layer, which layer protects the active agent against contact with the atmosphere and/or light. In such cases the protective layer must be impermeable to air and moisture and/or rendered opaque by the addition of dyes or pigments.

By building up the coating, it is possible to control the release of active agent following administration of the drug. For example, it is possible to place an active agent layer between at least two additional layers which control active agent resorption in the gastrointestinal tract. The layer of active agent can be arranged between two acid-insoluble layers, so that during administration, the dosage form passes through the stomach, with resorption of the drug taking place in the intestinal tract itself.

In a similar manner, it is also possible to apply different active agents in different layers in a superimposed manner on the carrier film, so that resorption takes place successively and/or in delayed form. Similar pharmacokinetic effects can also be obtained through the incorporation (e.g. suspension) of different pretreated, microencapsulated active agents.

The application of the active agent-containing coatings to the carrier, e.g. a release paper or release plastic film, preferably takes place with the aid of a smooth roll coating process. The coating substance preferably heated to approximately 60° to 80° C. is applied in a thin coating using a closed application system on a heated roller. With delayed synchronism in specific selectable ratios, the material can be transferred to a parallel roller, whereby a reduction of the coating thickness in a ratio 1:2 to 1:10 can take place, so that simultaneously the tolerances during application are reduced by these factors.

The coating of the carrier material takes place synchronously by means of a further roller system. On adapting the active agent coating material to the release value of the carrier material, there is no need to add an adhesive. However, optionally suitable adhesives can be added.

When applying several layers, as has been described hereinbefore, the layers are successively applied with each coating optionally directed to a drying station. This can comprise a thermostatically controlled pair of rollers and a drying tunnel controllable in sectional form. After the final drying process, the coated material is wound on to reels.

The active agent-containing coating is subsequently pre-split into dosage units, which can be removed in the same way as adhesive labels from the carrier material. Normally this pre-splitting or preliminary subdivision takes place at the drug manufacturers, but the coated material can be supplied to hospitals or pharmacists, where the preliminary subdivision takes place in dose-dependent manner or individually in accordance with the doctor's prescription.

Preliminary subdivision takes place in a particularly simple manner by punching. This stage can be combined with the printing of the carrier material. However, in many cases it is advantageous to carry out the printing of the carrier material prior to coating.

Before, or preferably after pre-splitting of the active agent-containing coating into dosage units, the coated carrier material is split into ready-for-use portions, which contain a given number of dosage units. The material can be cut into narrow strips on reels and individual dosage units removed in much the same way as individual adhesive labels.

The invention has been described hereinbefore in conjunction with drugs, but is in no way restricted thereto. For example, in the same way, it is possible to produce dosage forms for chemical reagents, flavouring agents and the like.

The following embodiments serve to further illustrate the invention:

EXAMPLE 1

Preparation of a Cardiac Dosage Form

For wet application to a release paper (siliconized paper with a weight per unit area of 100 g/m$^2$) a coating material was prepared in accordance with the following formulation:

| Gelatin | 10.0 parts by weight = 22.22% |
|---|---|
| Potato starch | 3.0 parts by weight = 6.67% |
| Glycerol | 1.5 parts by weight = 3.33% |
| Titanium dioxide | 0.3 parts by weight = 0.67% |
| α-Acetyldigoxin | 0.2 parts by weight = 0.44% |
| Water | 30.0 parts by weight = 66.67% |

This coating material was applied to the release paper in a coating thickness of 90 g/m$^2$ by means of rollers. After drying, the coating had a residual water content of 11.76%. The coating weight was 34 g/m$^2$, which represents a drug proportion of 0.4 g/m$^2$. A portion 2×2.5 cm=5 cm$^2$ (corresponding to the dimensions of a definite postage stamp) contained 0.2 mg of α-acetyldigoxin, which corresponds to the content of a commercially available tablet.

EXAMPLE 2

Preparation of a Contraceptive Dosage Form

For wet application to a release paper (110 g/m$^2$ paper siliconized on one side), a coating material with a slime-like consistency was prepared in accordance with the following formulation:

| Gelatin | 10.00 parts by weight = 22.22% |
|---|---|
| Corn starch | 3.17 parts by weight = 7.04% |
| Glycerol | 1.50 parts by weight = 3.33% |
| Titanium dioxide | 0.30 parts by weight = 0.67% |
| Levonorgestrel | 0.03 parts by weight = 0.07% |
| Water | 30.00 parts by weight = 66.66% |

The coating material was applied to the release paper with a coating weight of 45 g/m$^2$ using a roll transfer process. After drying, the coating had a residual water content of 11.76%. For a coating weight of 17 g/m$^2$, the medicament proportion was 0.03 g/m$^2$.

A portion of 2.5×4 cm or two portions of 2.5×2 cm=10 cm$^2$ consequently contains 0.03 mg of levonorgestrel, which corresponds to the content of a commercially available dragee.

What is claimed is:

1. A drug dosage form having homogeneity and galenic stability comprising:
   (i) a non-ingestible surface carrier material, and
   (ii) an active agent-containing coating disposed on a first surface of said carrier material, and wherein said coating is subdivided into removable oral dosage units.

2. A dosage form according to claim 1, wherein said carrier material is a plastic film or sheet, a thin metal foil, or a silicone- or wax-coated paper.

3. A dosage form according to claim 1, wherein said coating is cut or perforated into dosage units.

4. A dosage form according to claim 1, wherein said coating comprises more than one active agent.

5. A dosage form according to claim 1, wherein said coating further comprises water-soluble swelling substances.

6. A dosage form according to claim 1, wherein said coating comprises a plurality of layers comprising a first layer containing an active agent in contact with the carrier and at least one additional coating layer and optionally an intermediate layer free of an active agent interposed between said first and additional coating layer.

7. A dosage form according to claim 6, wherein incompatible active agents are present in said additional coating layer.

8. A dosage form according to claim 6, wherein an active agent-containing layer is arranged between at least two additional layers, whereby resorption of the active agents in the gastrointestinal tract is controlled.

9. A dosage form according to claim 6, wherein a layer is disposed over the active agent layer which layer is capable of protecting the active agent from contact with the environment of from exposure to light.

* * * * *